United States Patent [19]

Kuhn et al.

[11] Patent Number: 5,202,268
[45] Date of Patent: Apr. 13, 1993

[54] MULTI-LAYERED TEST CARD FOR THE DETERMINATION OF SUBSTANCES IN LIQUIDS

[75] Inventors: Raymond Kuhn, Clemmons; Gene H. MacDonald, Greensboro, both of N.C.

[73] Assignee: Environmental Diagnostics, Inc., Burlington, N.C.

[21] Appl. No.: 292,322

[22] Filed: Dec. 30, 1988

[51] Int. Cl.$^5$ .................................... G01N 33/553
[52] U.S. Cl. .................................... 436/525; 436/518; 436/810; 436/531; 435/174; 435/970; 422/100; 422/56; 422/58
[58] Field of Search .............. 436/525, 518–524, 436/526–531, 810; 422/55–57, 58, 100; 435/174, 970

[56] References Cited

U.S. PATENT DOCUMENTS

| | | | |
|---|---|---|---|
| 4,323,536 | 4/1982 | Columbus | 422/56 |
| 4,477,575 | 10/1984 | Vogel et al. | 422/56 |
| 4,727,019 | 2/1988 | Valkirs et al. | 435/5 |
| 4,775,636 | 10/1988 | Moeremans et al. | 436/518 |
| 4,959,305 | 9/1990 | Woodrum | 435/7 |
| 4,960,691 | 10/1990 | Gordon et al. | 435/6 |

*Primary Examiner*—Esther L. Kepplinger
*Assistant Examiner*—Donna C. Wortman

[57] ABSTRACT

A composite device for detecting or determining the presence of components in liquids is described. The device has, in combination at least a first and a second layer of porous material in contact with each other, at least one sample receiving site in said device and at least one reaction site connected to the sample receiving site via the second layer. A pre-determined liquid flow path in and through said layer is defined by liquid barrier means located in said layers whereby liquid deposited at the sample site is transferred to the reaction site along a path from one member to the other.

15 Claims, 2 Drawing Sheets

MULTI-LAYERED TEST CARD FOR THE DETERMINATION OF SUBSTANCES IN LIQUIDS

BACKGROUND OF THE INVENTION

This invention relates to a diagnostic test device for determining the presence of substances in liquid media. More specifically, it relates to the provision of a multi-layered test device for determining the presence of immunological, biological, enzymatic materials or other analytes in liquids especially biological, industrial or agricultural liquids. Still more specifically, it relates to the provision of a multi-layered device for the detection of such substances in a rapid manner and wherein the results thereof are determinable without a reading instrument.

GENERAL DESCRIPTION OF THE PRIOR ART

In the field of diagnostic testing, the art has evolved from the use of complex radioimmunoassays and enzyme immunoassays to the use of single card-type devices. In general, the art has sought to both increase the readability of such devices to eliminate the need for an instrument and to render the device readable in a shorter period of time so that one may make a determination of the analyte under field condition. The art has also attempted to shorten the number of steps that are required to conduct the test so that elements of simplicity and convenience are introduced into the test system.

The art would indeed benefit from a test device which is portable, develops a visual color change almost immediately upon the introduction of test sample, and is readable by the naked eye in a remote location without the need for instrumentation. The art would benefit from a system which eliminates the need for multiple steps in performing the test and specifically, from the elimination of multiple wash steps and long incubation times so that the time for reading the test could be shortened and the convenience could be amplified dramatically.

OBJECTS AND ADVANTAGES OF THE INVENTION

It is an object of the invention to provide a test device which can be employed at the site and in the field and at the immediate location where the substances are to be detected.

It is a further object of the invention to provide a diagnostic test device which following the addition of the sample requires little or no further intervention prior to the development of the reaction for the visualization of the end result.

It is an additional object of the invention to provide a test device having multi-layers and comprised of filter type planar membranes which incorporate therein binding materials at appropriate sites such as antibodies and/or antigens to facilitate the reaction mechanism. Other objects and advantages will be apparent from the following specification and the accompanying drawings.

GENERAL DESCRIPTION OF THE INVENTION

The invention provides a composite structure of porous materials wherein, through the selection of different pore sizes in appropriate areas of the structure and the juxtaposition of liquid barrier means, a liquid flow path is defined which results in an unexpected liquid flow force sufficient to cause a discernible change in an immunologic complex or in other reactions when appropriate materials are selected.

A commonly encountered problem in the field of immunoassay occurs when competitive or sandwich type binding assays are performed on a solid porous matrix. The immunological reaction in such procedures often does not occur rapidly enough nor conveniently visibly enough in the absence of several wash steps or reagent additions. Even with the additional steps, often times the reaction is not sufficiently visible within a convenient time to be useful.

In the typical competitive binding assay, an externally supplied tagged antigen competes with the antigen of a sample to react with an externally supplied antibody. (If the analyte is an antibody, the appropriate binding partners are chosen.) Each antigen molecule whether tagged or present in the sample has an opportunity to react with the supplied antibody and the extent to which they do react is a measure of the concentration of the antigen in the original sample. Such a system lends itself well to the present invention.

Theoretically, it is possible to perform a competitive assay by displacing tagged antigen from a tagged antigen/antibody complex by contacting the complex with antigen from the sample. Thus, if a tagged antigen/antibody complex were immobilized on a solid substrate, and that complex contacted with a source of untagged antigen, one might expect a displacement of the tagged antigen to occur. Unfortunately, when the solid substrate is a porous material, the mere contact as described above, does not always result in a displacement which is suitable for commercial analyte detection. Applicant has discovered a structure and technique which favors in a simple one step operation the displacement of tagged antigen from a tagged antigen/antibody complex by sample antigen (if the complex is originally configured and supplied in this manner) or the effective competition between the sample analyte and externally supplied tagged analyte for the immobilized capture binding partner with rapid revelation of a visual indication of such reaction.

Other forms of immunoassay formats such as sandwich reactions and competitive binding using a detection system for antibodies as the analyte rather than antigens as described, may also be employed as will be seen in the detailed description of the invention.

Briefly, and without regard to the drawings at this point, a structure is provided with a combination of various pore sizes and liquid flow barriers so as to produce rapid wicking of a sample in a pre-determined liquid flow direction to a reaction site at which the desired reaction takes place.

In its most generalized form, the present invention contemplates a structure having at least two planar, flat porous members in intimate contact with each other at their planar surfaces. The multi-layered device is configured in such a way that when a small amount, such as a drop or two, of a liquid test sample is placed onto or into a sample receiving site provided at the top member, the liquid is forced to travel transversely into the bottom member owing to the presence of liquid flow barriers placed or created adjacent to the sample receiving site. The sample receiving site may be a hole in the top member, or may be the top member itself appropriately shaped or confined in consideration of the type of test to be performed.

The device is configured in such a way as to force the flow of sample liquid from the sample receiving port or site along a pre-determined pathway to the bottom member and ultimately to a reaction site on the bottom or top member depending upon the pre-determined path selected. The sample liquid thus ultimately reaches the reaction site not by lateral flow from the sample receiving site, but rather by traversing the sample receiving site in or on the top member in a transverse flow into the second member and up into the top member. Usually, the reaction site is placed on the top member. It may be placed at the bottom member under appropriate circumstances.

The characteristics of the members can be varied in such a way as to create either a rapid pulling action from the top member and/or a pumping action due to differential wicking characteristics between the lower member and the top member. Sample flow in the second member which receives the sample from the sample receiving site is also restricted by barrier means which constrain the flow of liquid in the second member to a defined space and a direction of that flow up into the first member.

By this action there is facilitated a wide variety of potential reactions and reaction sites. For example, the analyte of the sample dropped onto a top member in a manner in which the sample is prevented from flowing laterally to any substantial degree across the top member but is constrained to flow transversely, can be ultimately transferred to a reaction site located on the top member. This reaction site (whether located on the top member or on the bottom member) may either have reagents deposited thereon or may be itself a receiving site for additional reagents either directly applied or directed through the same route as the original sample deposition. The present invention requires the placement of a defined sample receiving site juxtaposed with certain liquid flow barriers and a reaction site in a predetermined fashion so as to direct the flow of the sample liquid in the pre-selected fashion.

The versatility of the device of the present invention is quite wide. For example, the members themselves may be either hydrophilic or hydrophobic depending on the test characteristics and the analytes to be tested. For example, by appropriate choice of structure and composition of members, analyses of aqueous or non-aqueous samples may be performed. Non-aqueous samples containing organic solvent-based material may be employed with hydrophobic members in appropriate circumstances. The invention also permits the use of hydrophobic material with aqueous samples should personal preferences dictate. Examples of hydrophobic materials are glass fiber, certain nylons, TEFLON ® (polytetrafluoroethylene and fluorinated ethylene-propylene polymers) and polyvinyl chloride polymers. Examples of hydrophilic materials are paper, certain cellulose acetates, polyvinylidene difluoride, cellulose nitrate, polypropylene, certain microfiberglass compositions and the like.

A combination of members with different porosities and binding characteristics with the added capability of being either hydrophilic or hydrophobic provides in the device a) the ability to perform on both aqueous and nonaqueous samples, b) the binding of reactants on one or both of the members and at different sites in the flow path of sample or reagents, and c) through impermeable barriers or slots, the ability to differentially control flow rates.

In one form of an immunoassay, the sample is added to the sample port to hydrate a reactant in the bottom or lower member. The reactant may be a competing analyte bound to an indicator such as enzyme or colloidal gold. A binding (capture) antibody is in this case, located at the reaction site. The member may be protein-binding, if desired to retain the capture antibody. The lower member could be non-protein-binding in the region of the placement of the indicator conjugate but could be protein-binding at the terminus past the reaction site to retain reactants and prevent them from diffusing back to the reaction site.

In another assay, the bottom member could be initially protein binding and during manufacture have adhered thereto one or more enzymes for an assay to determine the presence of a substrate in a sample solution. The sample would move through the lower member contacting specific enzymes in a determined sequential manner to effect the production of a product which could then be observed at the reaction site.

It will be obvious to those skilled in the art that numerous modifications of immunoassay procedures can be performed on the device. These include but are not limited to competitive assays for small analytes, sandwich assays, and direct detection of reactants in samples. It will also be obvious that other nonimmunologically based assays, such as substrate and product detection, use of nucleic acid probes, lectins, or any other ligand-receptor pairs with various indicator systems can be performed on the device as well.

To illustrate further, when a liquid sample is applied to the sample site in or on the upper member, the liquid will wick by capillary action into the lower member in either a rapid fashion or slower fashion depending upon the characteristics of the member selected. It is preferred under certain circumstances that the lower member have a pore size substantially larger than the pore size of the upper member to facilitate a pumping action on the return flow from the bottom member to the top member. Sample is prevented from moving laterally from the sample receiving site because the edge of the sample site has been rendered impermeable by the installed barrier means. These barrier means may be compression sites, slots, discontinuities in the material, sonic or heat-generated barriers and the like and are all within the skill of the art to construct and place.

Once liquid enters the lower member it moves laterally and transversely until it contacts an impermeable barrier installed in the lower member and juxtaposed in such a way as to permit flow of liquid back up into the top member therein to come in contact with reagents or the like at a reaction site. The reaction site may contain the elements of an indicator system useful in detecting the analyte (or substrate) of interest. In addition, if desired, the reaction site may be located in the lower member with the top member serving as the remote site for accumulation of reactants and sample past the reaction site.

For example, in a preferred embodiment, wherein a competitive immunoassay is performed, the reaction site may conveniently contain antibodies (capture antibodies) to the analyte of interest, which said antibodies are covalently bonded or otherwise attached to the upper member. In this regard, if desired, a protein-binding type of member may be selected as the top member to facilitate the binding of the antibody. A conjugate of an indicator molecule attached to the analyte of interest is selected. A preferred conjugate is the analyte bound directly to colloidal gold if feasible, or to a carrier molecule if, for example, the analyte is unable or poorly able to bind to the gold itself. Colloidal gold is a well-known reagent used in diagnostic procedures because of its characteristic reddish color. As carrier molecules there may be employed for example, natural or synthetic proteins or other macromolecules such as BSA, poly L-Lysine, polysaccharides, histones, casein, horseradish peroxidase and the like. The conjugate may be admixed with the sample prior to applying the sample to the receiving site or may be installed in the device somewhere in the pre-determined liquid flow path prior to the reaction site. If the analyte in the sample is homologous to the analyte adhered to the colloidal gold, it will compete with the analyte-gold conjugate at the reaction site for the capture antibody. Assuming appropriate selection of antigen/analyte-gold conjugate concentration in consideration of the conditions of the assay, the analyte-gold conjugate will lose in the competition to the analyte in the sample, and no conjugate will remain bound to the capture antibody. The reaction can then be traced by the absence of the accumulation of gold at the reaction site. Thus, a positive reaction is signified by a lack of change of color at the reaction site (i.e., absence of conjugate). This reaction, normally termed a competitive binding assay, is typical of the ones that may be performed with the device of the present invention. Other formats may be used as well as will be described hereinafter.

The following is a brief description of the drawings presented herein from a consideration of which the present invention will be further understood.

DETAILED DESCRIPTION OF THE DRAWINGS

Figure 1:
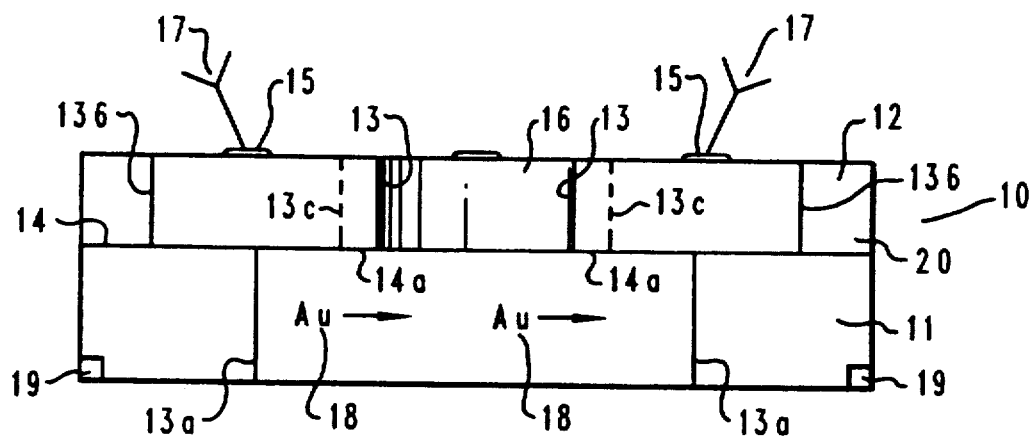
FIG. 1 is a cross-sectional view taken across the plane A—A of FIG. 2 of a device of the present invention.
Figure 2:
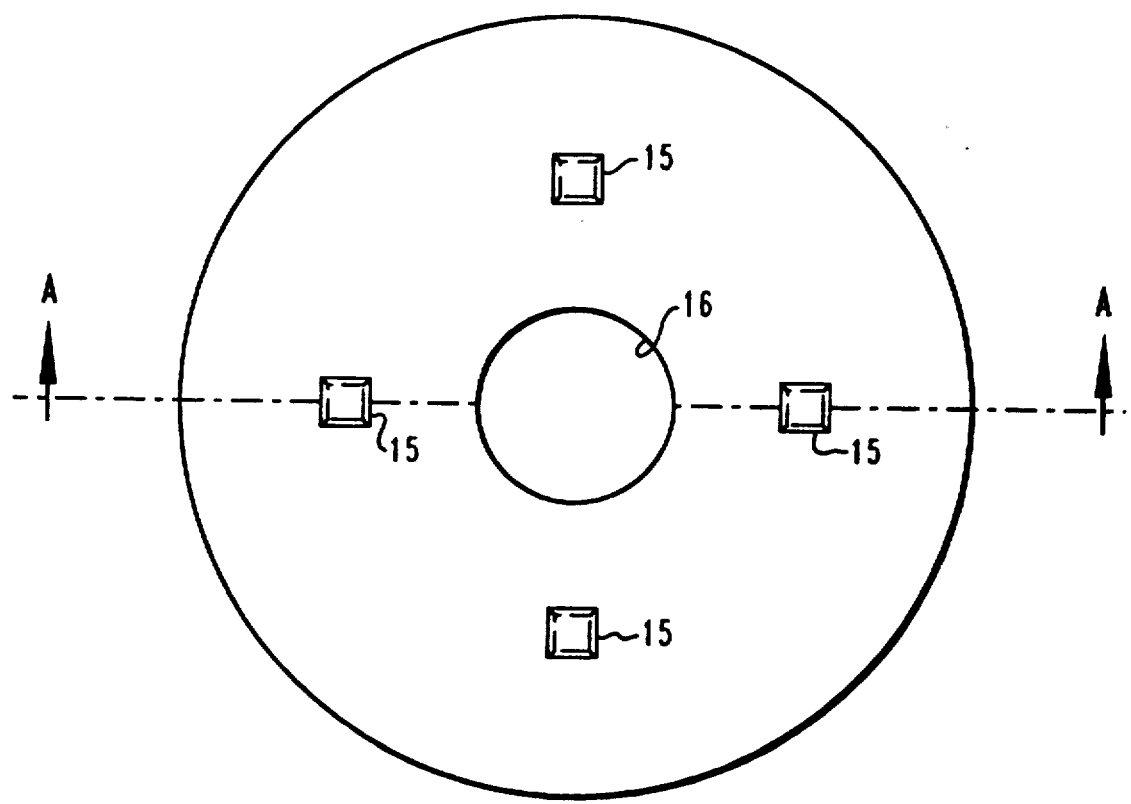
FIG. 2 is an embodiment of the device of the invention shown in circular form.

FIG. 1 shows a device of the present invention at 10 wherein a bilayered device is shown with two of the four reaction sites 15 shown in the plane of dissection A—A of FIG. 2. Upper layer 20 is provided with a sample port 16 and vent ports 19, and communicates with member 11 at interface 14. Bounding sample port 16 are barriers 13. Member 20 and member 11 may be the same or different material and may have the same or different porosities and/or the same or different wicking actions. In a preferred embodiment of the invention, the bottom layer has a pore size about 5 to 10 times greater than the pore size of the upper member and the pore size of the upper member is in the range of 0.2–0.75 microns.

With regard to the varying pore sizes, it should be noted that the larger pore size should not be so large as to provide a sink for the liquid, since this will frustrate the pumping action desired. What is highly desirable however is a pore size that results in a "push" of the sample through the sample port into the lower member followed by a "pull" (as will be described later) of the liquid from the lower member back into the first member.

Members 11 and 20 are also equipped with barriers 13a and 13b which are generally incorporated during the manufacturing process as by welding or by incorporation of slots, discontinuities or the like. Barriers 13b are incorporated to provide additional reservoir compartments and are optional depending on the size of the reservoir desired. Barriers 13c are also optional; in practice, the barrier at 13 is usually sufficient. There may be some circumstances, however, where the kinetics of the test and the device size are such that it would be desirable to direct the upward flow of liquid into the top member at a point somewhat remote from the sample receiving site. In such a case, barriers 13c may be provided and interface 14a rendered impermeable or not, as desired.

Present on member 20 are reaction sites 15 containing various reactants placed in accordance with and in consideration of the ultimate test that is to be performed. As shown in FIG. 2, these reaction sites may be more than one in number and may be for the same or different analytes coming from the same sample or may be for a control. The device 10 may also have either antibodies or antigens, but preferably in the discussion given herein, will have antibody 17 attached to the member 10 either by covalent bonding or some other physical or chemical attachment. There is also provided in member 11, at 18, a conjugate shown as Au→of colloidal gold or some other indicator system conjugated to an antigen which is specific: for or will react with the antibody at 17. Thus, in its completed composite form ready for use, there is a conjugate 18 of the gold (or other indicator system) to the antigen incorporated into the flow path of the device prior to the reaction site 15. Alternatively, the conjugate may be admixed with sample instead of being incorporated into the device, and the sample/conjugate mixture be allowed to follow the flow path to reaction site 15.

Instead of gold, there may be employed any other detection systems used in immunoassays such as enzymes, fluorescing agents, latex beads, luciferases, chemiluminescent agents and the like depending upon the best mode of reaction for the given analyte as determined by individual preferences.

In use, a liquid sample is dropped into sample port 16 and the sample allowed to diffuse into member 11 and mix with conjugate 18. Lateral flow is prevented by the barriers 13 which direct flow of the sample into the second member. Upon reaching the second member, the liquid is directed laterally until it reaches a barrier (e.g. 13a) or until it is not permitted to go any further and is "pulled" into member 20 in admixture with conjugate 18. The mixture then migrates to the reaction site 15. At the reaction site 15, if the sample contains analyte corresponding to the antigen which is conjugated to the indicator system, it will compete with the conjugate in reaction with antibody 17. If the sample contains no such antigen, then the only reactant at site 15 other than antibody 17 will be conjugate which will then react and show a color change. If sample does contain relevant antigen, the reaction at 15 will be almost exclusively due to the presence of such antigen because the concentration of conjugate and antibody 17 selected in constructing the device has deliberately been adjusted to favor reaction from the normally encountered concentration of analyte in the sample. Thus, a positive result is shown as no color change. For example, in FIG. 3 such a result is shown by an "S" for sample being attached to the antibody 17. The gold/antigen complex does not attach at reaction site 15 and is further removed from that area by the flow of liquid continuing past the reaction site and into the further reaches of members 20 and 11. If desired, larger amounts of reservoir type material can be supplied simply by extending member 20 laterally or providing additional reservoir space in member 11 depending upon how much reservoir space is needed as a function of the test that is being performed. Also, a reservoir of absorbent material may be placed in juxtaposition with member 20.

Figure 3:
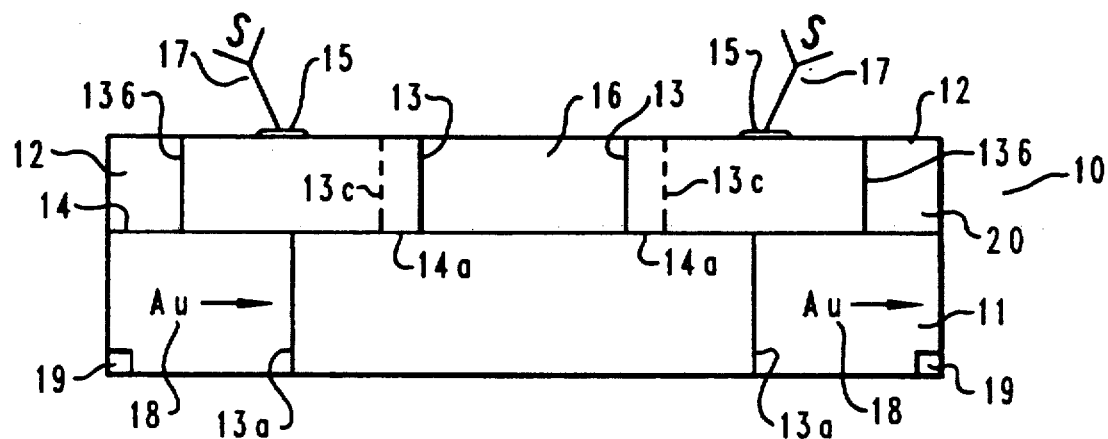
FIG. 3 is a device of the invention shown after it has been acted upon by a test liquid operating on the device of FIG. 1.

Following addition of the sample, it is desirable though not necessary in many cases, to add a wash solution to further direct the sample away from the reaction site so that any indicator antigen complex adjacent to the reaction site is moved further away as is evidenced by FIG. 3.

Figure 4:
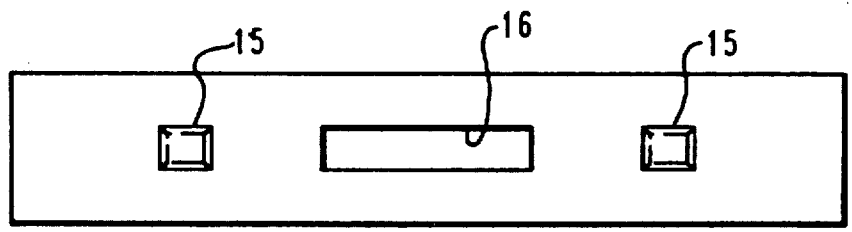
FIG. 4 is a top view of another embodiment of a device of the present invention.

If the reaction device as shown in FIG. 4 for example, is equipped with viewing ports so that the migration of the gold or indicator system away from the reaction site 15 is obscured, then a change in color at the reaction site 15 is all that one needs to observe. Sufficient wash material or sample may be applied to permit the visualization of the clear spot in the event that sample does contain the suspected analyte.

Although FIG. 2 has been shown as being circular in form, it may be of any convenient shape such as rectangular, cross-shaped or the like. In addition, it need not be restricted to one reaction site or sample receiving port but may include a variety and a plurality of either or both of those and may include reactants for detection of various analytes.

With respect to the material that may be employed as the members, particular success has been observed with polyvinylidene difluoride with pore sizes of about 0.2 to 0.75 microns for the top member and from 3-5 microns for the lower member. Various other materials may be employed such as cellulose acetates, cellulose nitrates, polypropylenes, certain microglass fiber compositions and the like.

Although the above description has been given with reference to a competitive binding assay wherein the analyte to be detected is an antigen and the immunoreagent at reaction site 15 is an antibody and the indicator system at 18 is gold complexed to an antigen which binds with the antibody, the present invention is also suitable for a competitive assay in which the analyte is an antibody to be determined instead of an antigen. Moreover, the present invention is also suitable for the detection of an antigen or antibody as an analyte wherein a sandwich technique is employed for the reaction. For example, in an immunoassay for human chorionic gonadotropin (hCG), gold conjugated to anti-beta hCG is placed in the bottom member at 18 (FIG. 1) and anti-alpha hCG (capture Ab) is covalently or otherwise attached to the upper member at 15. If sample contains hCG it binds to the gold/antibody conjugate and migrates to site 15 where the sample hCG part of the complex binds to the capture antibody (17) and yields a red color at site 15 indicating a positive result. If hCG is absent from the sample, the gold-anti-beta hCG complex has no hCG bound to it. The complex would not bind to capture antibody 17 but would instead migrate past the reaction site to the remote reaches of member 20 and/or member 11 (e.g. to 12 on member 20).

What is claimed is:

1. A composite device for detecting or determining the presence of components in liquids which comprises in combination at least a first and a second layer of porous material in contact with each other and having differential wicking characteristics, at least one sample receiving site in said device on said first layer, and at least one reaction site on said first layer said reaction site being distant from said sample receiving site and in communication with said sample receiving site via said second layer and a liquid flow path in and through said layers whereby liquid deposited at the sample site is transferred to the reaction site along a path from one layer to the other.

2. The device of claim 1 wherein the porous material is flat and planar.

3. The device of claim 2 wherein the porous material is nylon, polytetrafluoroethylene, fluorinated ethylene-propylene polymers, glass fibers, polyvinyl chloride, cellulose acetate, polyvinylidene difluoride, cellulose nitrate or polypropylene.

4. The device of claim 2 wherein each layer is hydrophobic, or each layer is hydrophilic, or either layer is hydrophobic and the other layer is hydrophilic.

5. The device of claim 1 wherein there is present at said at least one reaction site a binding partner of an immunologic component to be determined.

6. The device of claim 5 wherein there are present a plurality of reaction sites.

7. The device of claim 5 wherein the immunologic binding partner is an antibody and the component to be determined is an antigen.

8. The device of claim 7 wherein there is present in said second layer in the liquid flow path prior to the reaction site an antigen corresponding to the component to be determined which antigen is conjugated to an indicator system.

9. The device of claim 8 wherein the indicator system is colloidal gold.

10. The device of claim 7 wherein there is present in said second layer in the liquid flow path prior to the reaction site an antibody reactive with the antigen to be determined which antibody is conjugated to an indicator system.

11. The device of claim 10 wherein the indicator system is colloidal gold.

12. The device of claim 1 wherein the barriers are slots, discontinuities, welds, or compressions and are located in the liquid pathway so as to control flow direction and rates.

13. The device of claim 1 wherein there are present in said device in the liquid flow path prior to the reaction site reactants whereby when sufficient liquid flows along said pathway, said reactants are delivered to said reaction site.

14. The device of claim 12 wherein each layer is protein-binding or each layer is non-protein-binding or either layer is protein-binding and the other is non-protein-binding.

15. The device of claim 12 wherein each layer has the same or different porosities.

* * * * *

UNITED STATES PATENT AND TRADEMARK OFFICE
CERTIFICATE OF CORRECTION

PATENT NO. : 5,202,268
DATED : April 13, 1993
INVENTOR(S) : Kuhn et al

It is certified that error appears in the above-indentified patent and that said Letters Patent is hereby corrected as shown below:

Col. 8, line14, after "layers" insert -- defined by liquid barrier means located is said layers --.

In the drawings, Figs. 1 and 3, delete, in each, "136" and substitute therefor --13b--.

Signed and Sealed this

Twenty-ninth Day of March, 1994

Attest:

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO. : 5,202,268
DATED : April 13, 1993
INVENTOR(S) : Kuhn et al

It is certified that error appears in the above-indentified patent and that said Letters Patent is hereby corrected as shown below:

Col. 8, line 14, after "layers" insert -- defined by liquid barrier means located in said layers --.

In the drawings, Figs. 1 and 3, delete, in each, "136" and substitute therefor -- 13b --.

This certificate supersedes Certificate of Correction issued March 29, 1994.

Signed and Sealed this

Sixteenth Day of May, 1995

Attest:

BRUCE LEHMAN

Attesting Officer

Commissioner of Patents and Trademarks